(12) United States Patent
Purmal et al.

(10) Patent No.: US 6,617,100 B2
(45) Date of Patent: *Sep. 9, 2003

(54) SOLID PHASE QUENCHING SYSTEMS

(75) Inventors: Andrei A. Purmal, Waltham, MA (US); Samuel K. Ackerman, Weston, MA (US)

(73) Assignee: V.I. Technologies, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/260,375

(22) Filed: Mar. 1, 1999

(65) Prior Publication Data

US 2002/0123030 A1 Sep. 5, 2002

Related U.S. Application Data

(63) Continuation-in-part of application No. 09/161,078, filed on Sep. 25, 1998, now Pat. No. 6,403,359.

(51) Int. Cl.$^7$ ................................................. C12N 7/06
(52) U.S. Cl. ........................ 435/2; 435/235.1; 435/236; 435/238; 422/28; 422/30; 422/31; 210/660
(58) Field of Search ........................ 435/2, 235.1, 236, 435/238; 422/28, 30, 31; 210/660

(56) References Cited

U.S. PATENT DOCUMENTS

| | | |
|---|---|---|
| 3,487,157 A | 12/1969 | Pierce |
| 3,492,289 A | 1/1970 | Symm et al. ................ 260/239 |
| 3,501,557 A | 3/1970 | Brois et al. .................. 260/978 |
| 3,636,196 A | 1/1972 | Bauer et al. |
| 4,098,726 A | 7/1978 | Wagner et al. .............. 528/403 |
| 4,161,581 A | 7/1979 | Wagner et al. .............. 525/411 |
| 4,206,295 A | 6/1980 | Wagner et al. .............. 525/410 |
| 4,371,472 A | 2/1983 | Okazaki et al. ............. 260/453 |
| 4,429,045 A | 1/1984 | Bass et al. |
| 4,515,906 A | 5/1985 | Friesen et al. ................ 521/28 |
| 4,567,042 A | 1/1986 | Acree et al. |
| 4,581,368 A | 4/1986 | Ahmed et al. |
| 4,757,148 A | 7/1988 | Ahmed et al. |
| 4,784,992 A | 11/1988 | Reiner .......................... 514/77 |
| 4,841,023 A | 6/1989 | Horowitz ..................... 530/351 |
| 5,000,951 A | 3/1991 | Bass et al. .................. 424/89.9 |
| 5,055,485 A | 10/1991 | Geacintov et al. .......... 514/449 |
| 5,120,649 A | 6/1992 | Horowitz et al. ........... 435/173 |
| 5,232,844 A | 8/1993 | Horowitz et al. ......... 435/173.1 |
| 5,374,424 A | 12/1994 | Kelsey et al. ............. 424/202.1 |
| 5,418,130 A | 5/1995 | Platz et al. ..................... 435/2 |
| 5,547,576 A | 8/1996 | Onishi et al. |
| 5,559,250 A | 9/1996 | Cook et al. .................. 549/282 |
| 5,691,132 A | 11/1997 | Wollowitz et al. |
| 5,698,432 A | 12/1997 | Oxford ........................ 435/236 |
| 5,736,624 A | 4/1998 | Bieniarz et al. ............ 530/391.1 |
| 5,891,705 A | 4/1999 | Budowsky et al. |
| 6,093,564 A | 7/2000 | Budowsky et al. |
| 6,093,725 A | 7/2000 | Cook et al. |
| 6,114,108 A | 9/2000 | Budowsky |
| 6,136,586 A | 10/2000 | Budowsky |
| 6,270,952 B1 | 8/2001 | Cook et al. |
| 6,352,695 B1 | 3/2002 | Budowsky et al. |
| 6,369,048 B1 | 4/2002 | Budowsky et al. |
| 6,403,359 B1 | 6/2002 | Purmal et al. |
| 2002/0034724 A1 | 3/2002 | Edson et al. |
| 2002/0045228 A1 | 4/2002 | Hei |

FOREIGN PATENT DOCUMENTS

| | | |
|---|---|---|
| EP | 0 476 711 A2 | 3/1992 |
| EP | 0612532 A2 | 8/1994 |
| JP | 53-82735 | 7/1978 |
| JP | 6-80520 | 3/1994 |
| RO | 101400 | 4/1992 |
| SU | 1768636 A1 | 10/1992 |
| SU | 594771 A1 | 7/1993 |
| WO | WO 92/03157 | 3/1992 |
| WO | WO 92/04031 | 3/1992 |
| WO | WO 92/18161 | 10/1992 |
| WO | 96-39818 | * 12/1996 |
| WO | WO 96/39818 | 12/1996 |
| WO | 96-40857 | * 12/1996 |
| WO | WO 97/07674 | 3/1997 |
| WO | WO 98/45415 | 10/1998 |
| WO | WO 99/17802 | 4/1999 |
| WO | WO 99/34791 | 7/1999 |
| WO | WO 00/18412 | 4/2000 |
| WO | WO 00/18969 | 4/2000 |

OTHER PUBLICATIONS

Bahnemann, "Inactivation of viruses in serum with binary ethyleneimine" *J. Clin. Microbiol.* 3:209–210 (1975).

Bahnemann, "Inactivation of viral antigens for vaccine preparation with particular reference to the application of binary ethylenimine" *Vaccine* 8:299–303 (1990).

Bieniarz et al., "A facile, high–yielding method for the conversion of halides to mercaptans" *Tetrahedron Lett.* 34:939–942 (1993).

Budowsky et al., "Inactivation of the phage MS2 infectivity by the action of ethyleneimines" *Biorg. Khim.* 11:989–991 (1985) (in Russian). English Abstract provided, 1 page.

Budowsky and Zalesskaya, "Principles of selective inactivation of viral genome. V. Rational selection of conditions for inactivation of the viral suspension infectivity to a given extent by the action of B–propiolactone" *Vaccine* 9:319–325 (1991).

(List continued on next page.)

*Primary Examiner*—Leon B. Lankford, Jr.
(74) *Attorney, Agent, or Firm*—Wolf, Greenfield & Sacks, P.C.

(57) ABSTRACT

The invention features a method of inactivating a contaminant, such as a virus, of a biological composition. The method includes the steps of: (a) contacting the biological composition with an inactivating agent including an aziridino moiety or a haloderivative salt thereof, where a portion of the agent reacts with and inactivates the contaminant, and a portion of the agent remains unreacted; (b) contacting the product of step (a) with a composition which includes one quenching moiety under conditions and for a time sufficient to allow the inactivating agent to bond covalently to the quenching moiety; and (c) separating the quenching moiety and the quenched inactivating agent from the biological composition.

19 Claims, 3 Drawing Sheets

OTHER PUBLICATIONS

Budowsky et al., "Principles of selective inactivation of the viral genome; dependence of the rate of viral RNA modification on the number of protonizable groups in ethyleneimine oligomer" *Vaccine Res.* 5:29–39 (1996).

Creech et al., "Antitumor and mutagenic properties of a variety of heterocyclic nitrogen and sulfur mustards" *Med. Chem.* 15:739–746 (1972).

Dermer and Ham, Ethyleneimine And Other Aziridines, Acad. Press, NY—London (1969), pp. 249–285.

Earley et al., "Reactions of ethylenimines. IX. The mechanisms of ring openings of ethylenimines in acidic solutions" *J. Am. Chem. Soc.* 80:3458–3462 (1958).

Hagen et al., "Chemical modification of polystyrene introduction of sulfinate and sufone functionalities" *Polymer Bull.* 5:111–116 (1981).

King, "Evaluation of different methods of inactivation of newcastle disease virus and avian influenza virus in egg fluids and serum" *Avian Diseases* 35:505–514 (1991).

Kochetkov and Budowsky eds., *Organic Chemistry of Nucleic Acids, Part A*, Plenum Press, London–New York, pp. 48–55 (1972).

Kostyanovskii et al., "Oligomers of azridines and N–beta–azridinoethylamides," *Bull. Acad. Sci. USSR, Div. Chem. Sci.* 37:2315–2325 (1989). (Translated from IzvestiyaAkademi Nauk SSSR, Seriya Khimicheskaya 11:2566–2575.).

Prodouz et al., "Inhibition of merocyanine 540–mediated photosensitization of platelets and viruses" *Transfusion* 31:415–422 (1991).

Race et al., "An experimental chemically inactivated HIV–1 vaccine induces antibodies that neutralize homologous and heterologous viruses" *Vaccine* 13:54–60 (1995).

Tanirbergenov et al., "Regularities of mutagenic and toxic effects of ethyleneimine and its oligomers. A comparative study in the automated system SOS–chromotest and in standard bacterial test systems" *Genetika* 24:763 (1988) (in Russian). English translation provided, 5 pages.

Thanei–Wyss, "Interaction of quaternary ammonium compounds with acetylcholinesterase: characteristics of the active site" *Eur. J. Pharmacol., Mol. Pharmacol. Sect.* 172:165–173 (1989).

Twomey et al., "Structure and immunogenicity of experimental foot–and–mouth disease and poliomyelitis" *Vaccine* 13:1603–1610 (1995).

Van Etten and Dolhum, "Effects of hydrogen–bond formation by phenols on the conformational equilibrium of trans–1,2–dimethyl–3–isopropylaziridine" *J. Org. Chem.* 33:3904–3907 (1968).

Wagner et al., "Approaches to the reduction of viral infectivity in cellular blood components and single donor plasma" *Transfusion Med. Rev.* 5:18–32 (1991).

Ackerman et al., "INACTINE™–A Potent and Selective Method for Inactivating Viruses in Contaminated Blood Products," Vox Sanguinis 74(S1) 1305 (1998).

Ackerman, et al., "INACTINE™–A Viral Inactivation Technology for Reducing the Infectivity of Plasma–Derived Proteins," Abstract presented at the 5$^{th}$ Annual Blood Safety and Screening Conference, McLean, VA, Feb. 22, 1999.

Amor et al., "Use of N–Acetylethyleneimine [AEI] for the Inactivation of Semliki Forest Virus In Vitro," Journal of Medical Virology 19:367–376 (1986).

Budowsky, "Problems and Prospects for Preparation of Killed Antiviral Vaccines," Advances in Virus Research 39:255–290 (1991).

Edson, "INACTINE™–An Inactivation Technology for Reducing the Viral Infectivity of Plasma–Derived Proteins and Red Blood Cells," Abstract from the IBC 2$^{nd}$ International Symposium on Viral Clearance, Jun. 25, 1998.

Edson et al., "INACTINE™–A Viral Inactivation Technology for Reducing the Infectivity of Plasma–Derived Proteins," Transfusion 38 (10S):75S S277 (1998).

Hassanain, "Preliminary Findings for an Inactivated African Horsesickness Vaccine Using Binary Ethyleneimine," Revue Elev. Med. vet. Pays trop., 45(3–4):231–234 (1992).

Lobastov, "Use of Ethylenimine Dimer for the Inactivation of Infectious Rhinotracheitis Virus of Cattle," Probl. Virusol., Mol. Biol. Gistol. S–kh. Zhivotn. pp. 4–6 (1983) translation attached.

Zalesskaya, "Inactivation of Viral Genome by Beta–Propiolactone and Ethyleneimines Using the Bacteriophage MS–2 as an Example," Russian State Library, Moscow, Russia, 1988 translation attached.

Zhang et al., "INACTINE™–A Method for Viral Inactivation in Red Blood Cell Concentrate," Transfusion 38 (10S):75S S279 (1998).

Atwell, G. J. et al., Synthesis, DNA Interactions and Biological Activity of DNA Minor Groove Targeted Polyberizamide–linked Nitrogen Mustards, Bloorg Med. Client. 1995 Jun.; 3(6):679–91.

Briel, S. et al Identification of New Aqueous Chemical Degradation Products of Isophosphoramide Mustard J Pharm Biomed Anal. 2001 Jun; 25 (3–4): 669–78.

Brown, F. et al. A Universal Virus Inactivant for Decontaminating Blood and Biopharmaceutical Products Biologicals (1998) 26, 39–47.

Burrage, et al. "Inactivation of viruses by Aziridines", Advances in Transfusion Safety. Dev. Biol. Basel, Karger, 1999, vol. 102, pp. 131–139.

Charache, S. et al.. Evaluation of Extracorporeal Alkylation of Red Cells as a Potential Treatment for Sickle Cell Anemia, Blood 1976; 47(3):481–88.

Danao, T. et al., Nitrogen Mustard as Induction Therapy for Rheurnatoid Arthritis: Clinical and Immunologic Effects. J. Rheum. 1992 19:1683–86.

Drake, M.E. et al., Effect of Nitrogen Mustard on Virus of Serum Heptitiis in Whole Blood. Proc. of Soc. Exp. Rio. Med. 1952(80)310–13.

Ferguson, L.R. et al.. DNA–directed Aniline Mustards with High Selectivity for Adenine or Guanine Bases: Mutagenesis in a variety of Salmonella Tpyhimurium Strains Differing in DNA–Repair Capability,' Mutant Res. 1994 Apr.; 321(1–2):27–34.

Ferguson, L.R. et cal.. Bacterial Mutagenicity Studies of DNA–Intercalating Aniline Mustards: an Insight Into the Mode of Action of a Class of Anti–Tumor Drugs, Anticancer Drug Des. 1989 Oct.; 4(3):209–19.

Fries, K.M. et al 31P NMR and Chloride Ion Kinetics of Alkylating Monoester Phosphoramidates J. Med. Chem 1991 Feb; 34(2): 565–9.

Logrippo, G.A. et al.. Chemical and Combined Methods for Plasma Sterilization., 6th Congress of the Int'l Soc. of Blood Trans., 1958, pp. 225–230.

Gourdie T.A. et al.. Synthesis and Evaluation of DNA–targeted Spatially Separated Bis(Aniline Mustards) as Potential Alkylating Agents with Enhances DNA Cross–linking Capability, J. Med. Chem. 1991 Jan; 34(1):240–8.

Gravatt, G.L. et al., DNA–Directed Alkylating Agents 4. 4–Anilinoduinoline–Based Minor Groove Directed Aniline Mustards, J. Med Chem 1991, 34(5):1552–60.

Gravatt, G.L. et al., DNA–directed Alkylating Agents. 6. Synthesis and Antitumor Activity of DNA Tumor Groove–targeted Aniline Mustard Analogues of Pibenzimol, J. Med. Chem.. 1994 Dec. 9; 37(25): 4338–45.

Griffin M.T. et al Kinetics of Activation and in Vivo Muscarinic Receptor Binding of N–(2–bromoethyl)–4–Piperidinyl Diphenylacetate: an Analog of 4–DAMP Mustard J. Pharmacol Exp Ther 1993 Jul; 266(1) 301–5.

Hamza, A. Quantum Molecular Modeling of the Interaction Between Guanine and Alkylating Agents Nrogen Mustards, J. Med Chem 1991, 34(5):1552–60.

Hartman, F.W. et al., Preparation and Sterilization of Blood Plasma. Proc

Hartman, F.W. et al.. On the Chemical Sterilization of Blood and Blood Plasma. Proc. of Socc.. Exp. Bio. Med. 1949;70:248–54.

Hartman, F.W., et al.. Four–Year Study Concerning the Inactivation of Viruses in Blood and Plasma, Presented at the 55th Annual Meeting of the American Gastroenterological Association, San Francisco, California, Jun. 1954.

Hemminki, K. DNA Adducts of Nitrogen Mustards and Ethyleneimines DNA Adducts: Identification and Biological Significance, IARC Scientific Publications No. 125, Editors: Hemminki, et al., 1994, 99. 313–321.;.

Hemmiki, K. Reactions of Nitrogen Mustards with DNA IARC Sci. Publ 1986; (78):55–70.

Knorre, D.G. et al.. Reactive Derivatives of Oligonucleotides as Potential Antiviral Drugs, Problems of Virology, 1985, No. 5, pp. 524–'?.

Kohn, K.W. et al Mechanisms of DNA Sequence Selective Alkylation of Guanine–N7 Positions by Nitrogen Mustards Biochem Pharmacol 1988 May 1; 37(9): 1799–800.

Lee, M et al., In Vitro Cytotoxicity of GC Sequence Directed Alkylating Agents Related to Distamycin, J. Med.. Cheer, 1993, Apr. 2; 36(7)863–70.

Mattes, W.B. et al., GC–rich Regions in Genomes as Targets for DNA Alkylation, Carcinogenesis 1988; 9(11):2065–72.

Prakash, A.S. et al., Differences in Sequence Selectivity of DNA Alkylation by Isomeric Intercalating Aniline Mustards, Chem. Biol. Interact. 1990; 76(23):241–8.

Price, C.C. et al Relative Reactivities for Monofunctional Nitrogen Mustard Alkylation of Nucleic Acid Components Biochim Biophys Acta 1968 Sep 24; 166(2):327–59.

Roth, E.F. Jr. et al., Metabolic Effects of Antisickling Amounts of Nitrogen and Nor–N itrogen Mustard on Rabbit and Human Erythrocytes. Blood 1975;45(6):779–88.

Springer, J.B. et al Isophosphoramide Mustard and Its Mechanism of Bisalkylation J. Org. Chem 1998 Oct. 16; 63(21):7218–7222.

Valu, K.K. et al., DNA–directed Alkylating Agents. 3. Structure–activity relationships for Acridine–linked Aniline Mustards: Consequences of Varying the Length of the Linker Chain. J. Med. Chem 1990 Nov: 33(11):3014–9.

Verschaeve, L. et a. "Mutagenicity of Ethyleneimine" Mutation Res. 238:39–55 (1990).

Vlasov, V.V. et al., –The Feasibility, Of Blocking Influenza Infections by Means of Alkylating Derivatives of Oligonucleotides, Molecular Genetics, Microbiology, and Virology, 1984, No. 11.

Warrington, Derivatives of Aziridine as Inactivants for Foot–and–Mouth Disease Virus Vaccines Am J. Vet. Res., vol. 34, No. 8. pp. 1087–1091.

Wickham, G. et al., DNA–binding Properties and Antitumour Activity of Monofunctional Alkylating Groups Attached to the DNA–intercalating Chromophore Phenanthridine: n–Brotnoalkylplienanthridinium Bromides, Biochimic ct Biophysica Aeta 1991 1073:528–37.

Wilke, W.S. et cal., Parenteral Nitrogen Mustard for Inflammatory Arthritis, C'lev. Clin. J. Med. 1990 Oct.; 57(7):643–46.

Yamamoto, et al. Cancer Research 26, pt. 1, 2301–2306 (Nov. 1966).

Yang, C. et al The Preparation of an Inactivated Antigen for Bluetongue Serology Zentralbl Veterinarmed [B] 1984 Mat; 31(4);290–6.

* cited by examiner

Preparation of solid-phase quencher containing thiophosphate groups

Preparation of solid-phase quencher with high loading of thiophosphate groups

Quenching of aziridino-compounds by solid-phase bound thiophosphate

SOLID PHASE QUENCHING SYSTEMS

CROSS-REFERENCE TO RELATED APPLICATIONS

This application is a continuation-in-part of U.S. Ser. No. 09/161,078, filed Sep. 25, 1998 now U.S. Pat. No. 6,403,359.

BACKGROUND OF THE INVENTION

The invention relates to methods for quenching electrophiles.

The transmission of viral diseases (e.g., hepatitis A, B, and C, acquired immunodeficiency syndrome, and cytomegalovirus infections) by blood or blood products is a significant problem in medicine. Other biological compositions, such as mammalian and hybridoma cell lines, products of cell lines, milk, colostrum, and sperm, can also contain infectious viruses. Screening donor biological compositions for viral markers can help reduce the transmission of viruses to recipients, but many screening methods are directed to only a few discrete viruses, and are therefore incomplete, and may also be less than 100% sensitive. It is therefore important to inactivate viruses contained in donor blood, blood products, or other biological compositions.

A number of agents that are capable of inactivating viruses in blood have been developed. For example, ethyleneimine monomer and ethyleneimine oligomers (including dimers, trimers, and tetramers) are very effective viral inactivating agents. Methods for using ethyleneimine oligomers for inactivating viruses in biological compositions are described in U.S. Ser. No. 09/005,606 (filed Jan. 12, 1998), hereby incorporated by reference. Ethyleneimine oligomers are themselves chemically active, and must therefore be rendered non-reactive before a product, such as blood, is used clinically. Typically, a viral inactivating compound, such as ethyleneimine dimer, is added to a biological composition to inactivate infectious viruses that might be present in the composition. A quenching agent is then added to inactivate the ethyleneimine dimer that remains after viral inactivation has taken place. The end result is a biological composition that is relatively free of infectious viruses, but that is contaminated with quenched inactivating agent and with quenching agent.

SUMMARY OF THE INVENTION

In one aspect, the invention features a method of inactivating a contaminant of a biological composition. The method includes the steps of: (a) contacting the biological composition with an inactivating agent including an aziridino moiety or a haloderivative salt thereof, where a portion of the agent reacts with and inactivates the contaminant, and a portion of the agent remains unreacted; (b) contacting the product of step (a) with a quenching agent which includes a quenching moiety under conditions and for a time sufficient to allow the inactivating agent to bond covalently to the quenching moiety; and (c) separating the quenching agent and the quenched inactivating agent from the biological composition.

In a second aspect, the invention features a method of inactivating a contaminant of a biological composition. The method includes the steps of: (a) contacting the biological composition with an inactivating agent including an aziridino moiety or a haloderivative salt thereof, where a portion of the agent reacts with and inactivates the contaminant, and a portion of the agent remains unreacted; (b) contacting the product of step (a) with a quenching moiety, attached to a separation moiety through covalent bonds, under conditions and for a time sufficient to allow the inactivating agent to bond covalently to the quenching moiety; and (c) separating the separation moiety, the quenching moiety and the quenched inactivating agent from the biological composition.

A preferred quenching moiety of the first or second aspect includes a nucleophilic moiety, such as a thiophosphate or thiosulfate moiety; the thiophosphate moiety may be part of an internucleotide linkage of an oligonucleotide sequence.

Inactivating agents of the first or second aspect may be, for example, ethyleneimine, an ethyleneimine oligomer, a haloderivative salt of ethyleneimine, or a haloderivative salt of an ethyleneimine oligomer. A preferred inactivating agent is N-acetylethyleneimine. The biological composition may be selected from the group consisting of whole mammalian blood, purified or partially purified blood proteins, blood cell proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture supernatant, a placental extract, a product of fermentation, a platelet concentrate, a leukocyte concentrate, semen, red blood cells, and a recombinant protein-containing composition produced in a transgenic mammal. Preferably, the biological composition is whole human blood or human blood plasma. The contaminant may be a virus.

A preferred separation moiety is selected from the group consisting of a bead, a resin, an antibody, and a biotin molecule. The composition of the second aspect preferably also includes a reporter moiety selected from the group consisting of a UV adsorbing moiety and a fluorescent moiety.

In a third aspect, the invention features a method of quenching an electrophile. The method includes contacting the electrophile with a composition including a thiosulfate or thiophosphate moiety attached to a separation moiety, under conditions and for a time sufficient to allow the electrophile to bond covalently to the thiosulfate or thiophosphate moiety.

Preferably, the electrophile includes an aziridino moiety or a haloderivative salt thereof. For example, the electrophile may be ethyleneimine, an ethyleneimine oligomer, a haloderivative salt of ethyleneimine, or a haloderivative salt of an ethyleneimine oligomer. A preferred electrophile is N-acetylethyleneimine. Preferably, the separation moiety is selected from the group consisting of a bead, a resin, an antibody, and a biotin molecule. The composition may further include a reporter moiety, such as a UV adsorbing or fluorescent moiety. The thiophosphate moiety may be part of an internucleotide linkage of an oligonucleotide sequence.

In a fourth aspect, the invention features a method of removing a viral inactivating agent from a biological composition. The method includes the steps of: (a) contacting the inactivating agent with a quenching moiety that is coupled to a separation moiety selected from the group consisting of a bead, a resin, an antibody, and a biotin molecule; and (b) removing the inactivating agent, the quenching moiety, and the separation moiety from the biological composition. Preferably, step (a) includes contacting the inactivating agent with the quenching moiety under conditions and for a time sufficient to allow covalent bonds to form between the inactivating agent and the quenching moiety. A preferred quenching moiety includes a nucleophilic moiety, such as a thiosulfate or thiophosphate moiety.

In a fifth aspect, the invention features a compound which includes (a) a separation moiety; and (b) a thiosulfate or thiophosphate moiety. Preferably, the separation moiety is selected from the group consisting of a bead, a resin, an antibody, and a biotin molecule. The compound may further include a reporter moiety, such as a UV adsorbing or fluorescent group. The thiophosphate moiety may be part of an internucleotide linkage of an oligonucleotide sequence.

By "biological composition" is meant a composition that contains biological macromolecules, such as proteins, nucleic acids, lipids, and carbohydrates.

By "quenching moiety" or "quenching agent" is meant a moiety or an agent that is capable of reacting with, and thereby reducing the reactivity of, an electrophilic compound.

By "reporter moiety" is meant a UV adsorbing or fluorescent group which is added to the quenching agent for the monitoring of removal of the quenching agent and the quenched inactivating agent.

By "separation moiety" is meant a moiety which confers to a compound at least one property which allows for its separation from most other compounds in a biological composition. Preferred properties include selective high-affinity to a compound not normally present in the biological composition, the ability of the moiety to be separated from the biological composition through filtration, centrifugation, or placement in a magnetic field. A bead, a resin, an antibody, and a biotin molecule are each a preferred separation moiety.

The invention provides new methods for the quenching of viral inactivating agents and the subsequent removal of the quenching and inactivating agents from a biological composition. This method results in a biological composition that is relatively free not only of contaminating viruses, but also relatively free of quenched (i.e., non-reactive) inactivating agent and unreacted quenching agent. The invention provides methods which are compatible with methods of removing solvent and detergent from protein-containing preparations which are virally-inactivated by a solvent/detergent method.

Other features and advantages of the invention will be apparent from the following description and from the claims.

DETAILED DESCRIPTION

The invention provides general methods for quenching electrophiles with nucleophilic quenching agents, such as thiosulfate or thiophosphate moieties, that are modified so as to allow for the removal of the electrophile and the quenching agent from a biological composition.

Figure 2:
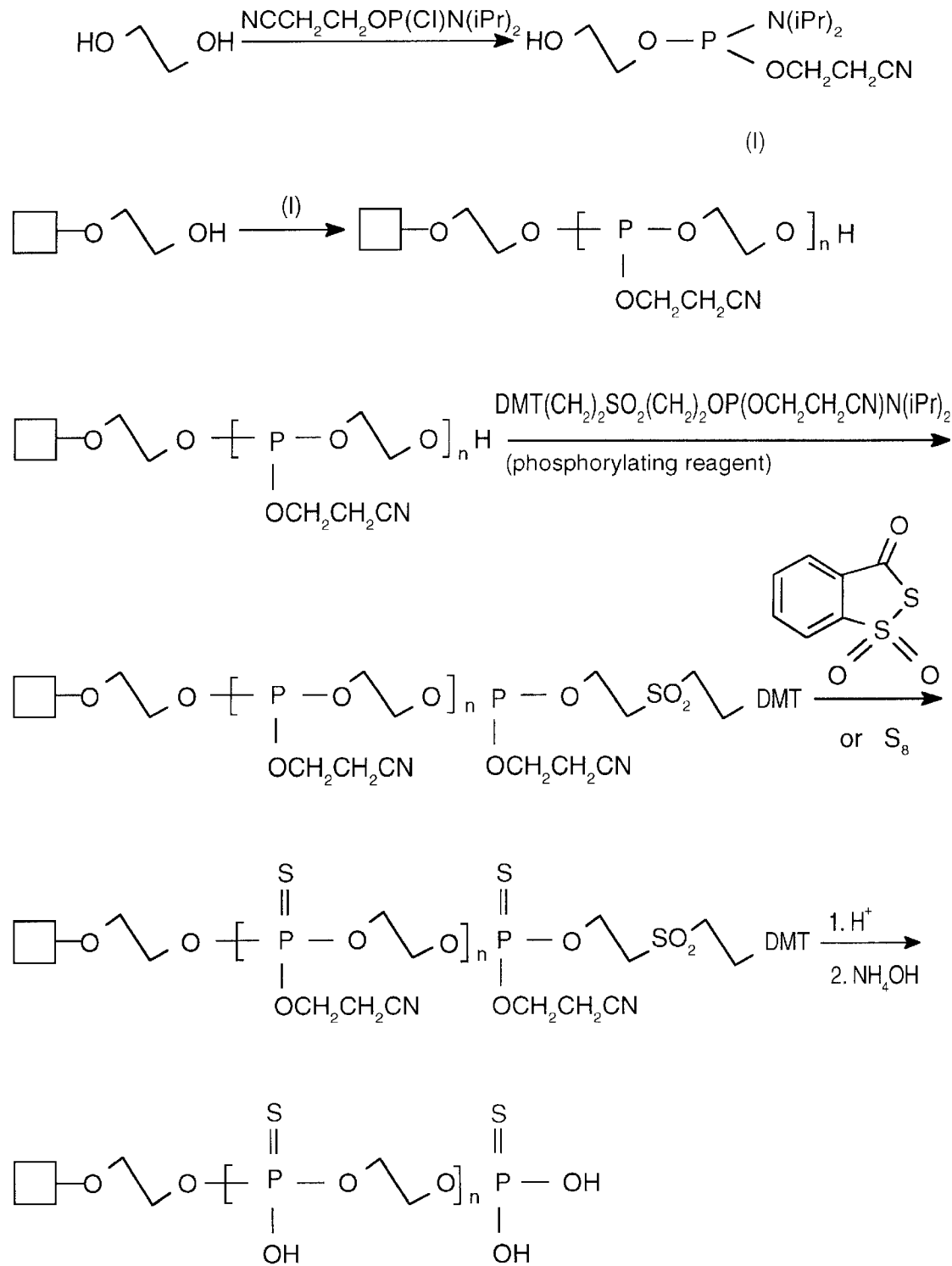
FIG. 2 is a schematic diagram outlining the preparation of a solid-phase quenching agent that contains multiple thiophosphate groups.
Figure 3:
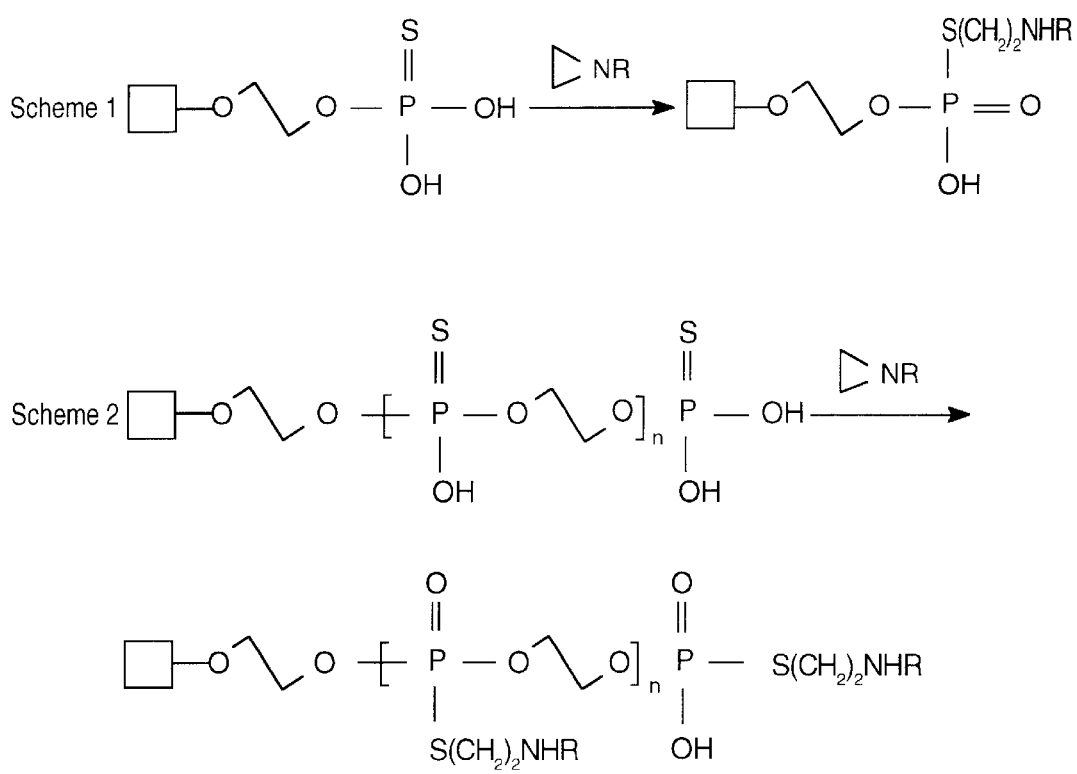
FIG. 3 is a schematic diagram depicting the quenching of an aziridino compound with a thiophosphate group that is covalently bonded to a Sepharose® (Pharmacia) bead.

A method of removal of quenching agent and quenched virus inactivating agent from a biological composition is through the use of nucleophiles, such as thiosulfate or thiophosphate groups, which have attached to them a second moiety (the separation moiety) which supplies particular properties to the quenching agent, such that the quenching agent can be completely and reliably separated, along with the quenched inactivating agent, from the biological composition. These modified quenching compounds can react with and quench electrophiles such as an ethyleneimine oligomer or N-acetylethyleneimine. This method has the added advantage that it is compatible with methods to remove solvent and detergent from protein-containing preparations which are virally-inactivated by the Solvent/Detergent procedure described by Budowsky et al., U.S. Ser. No. 09/005,719. The Solvent/Detergent method of virus activation is compatible with the virus inactivation by compounds such as ethyleneimine monomer and ethyleneimine oligomer. Thus, one can perform two methods of viral inactivation in sequence. Alternatively, the inactivation of viruses through the use of, for example, ethyleneimine oligomer, followed by quenching and removal of the quenching and inactivating agents using the methods described herein, can be performed without the use of the Solvent/Detergent method. It is also advantageous that the quenching agent be easily detectable in order to monitor its removal. In the examples provided in FIG. 2, this is fulfilled with the addition of thymidine, which is readily detected by its adsorbance of 260 nm light.

The thiophosphate groups used in the invention may be substituted with one substituent (e.g., [separation moiety]-OP($=$S)(OH)$_2$, also referred to as a thiophosphomonoester), substituted with two substituents (e.g., [separation moiety]-OP($=$S)(OH)(OAlk), a thiophosphodiester), or substituted with three substituents (e.g., [separation moiety]-OP($=$S)(OAlk)$_2$, a phosphothiotriester). The substituent may be, for example, a linear, branched, or cyclic saturated or unsaturated hydrocarbon with one to forty carbons, a benzyl group, a polycyclic aromatic group, an unsubstituted alkyl group, or an alkyl group substituted with hydroxyl, amino, azido, or cyano groups.

Polythiophosphate moieties (i.e., moieties having two or more adjacent phosphate groups) can also be used in the invention. For example, guanosine diphosphate (GDP) or guanosine triphosphate (GTP), in which one or more of the phosphate groups is a thiophosphate group, may be used in the invention. In the case of guanosine diphosphate, one or both phosphate groups may be thiophosphate groups. In the case of guanosine triphosphate, one, two, or all three of the phosphate groups may be thiophosphate groups. GDP or GTP may be attached to the separation moiety, for example, at the 2' or the 3' hydroxyl group or to the heterocyclic base.

The compositions of the invention can be prepared as described below in the Examples. They can also be prepared using other standard synthetic techniques of oligonucleotide synthesis, such as those described in *Oligonucleotides and Analogs: A Practical Approach* (Eckstein ed., IRL Press 1991).

The quenching systems of the invention can be used as follows. A viral inactivating agent, such as an ethyleneimine oligomer, is added to a biological composition, as described in Budowsky, U.S. Ser. No. 08/855,378 and Budowsky et al., U.S. Ser. No. 09/005,606. At the end of the time necessary for viral inactivation, the biological composition is contacted with quenching agent, a compound containing one or more thiosulfate or thiophosphate moieties attached to a separation moiety. The biological composition and the quenching agent are allowed to remain in contact for at least one hour, at room temperature and a pH of 7.0. A 10-fold excess of thiosulfate or thiophosphate groups per equivalent of ethyleneimine oligomer is used.

The thiosulfate or thiophosphate moieties react with the highly reactive moieties of the ethyleneimine compounds or their haloderivative salts, and become covalently linked to these compounds. When the coupled thiosulfate or thiophosphate moieties are removed from the biological composition, therefore, the quenched ethyleneimine compounds are removed as well. The end result is a biological composition that is substantially free of infectious viruses, quenched ethyleneimine compounds, and quenching agent.

For example, a biological composition containing the inactivating agent ethyleneimine dimer can be quenched with sodium thiosulfate. Methods for inactivating viruses in biological matrices and quenching with thiosulfate are well known in the art and are described, for example, in Budowsky, U.S. Ser. No. 08/835,446. The thiosulfate reacts with the aziridine ring and remains covalently bound to the quenched ethyleneimine dimer.

The biological composition may include any of a number of substances. Examples of compositions include whole mammalian blood, purified or partially purified blood proteins, blood cell proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture supernatant, a placental extract, a product of fermentation, a platelet concentrate, a leukocyte concentrate, semen, and red blood cells. Other biological compositions include those containing recombinant proteins produced in transgenic mammals. For example, the biological composition may include a protein that has been expressed in the milk of a transgenic mammal. Methods for producing such proteins are described, for example, in Wright et al., *BioTechnology* 9:830–834 (1991) and the references cited therein.

There now follow particular examples that describe the preparation of quenching systems of the invention and the use of these systems to quench viral inactivating agents. These examples are provided for the purpose of illustrating the invention, and should not be construed as limiting.

EXAMPLE 1

Figure 1:
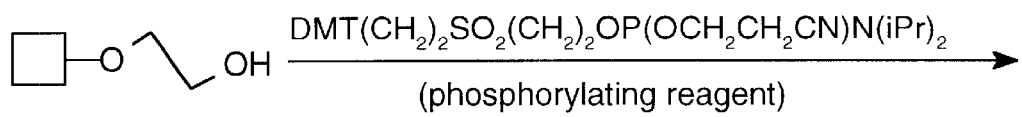
FIG. 1 is a schematic diagram outlining the preparation of a solid-phase quenching agent that contains a thiophosphate moiety linked to a separation moiety.
Figure 1:
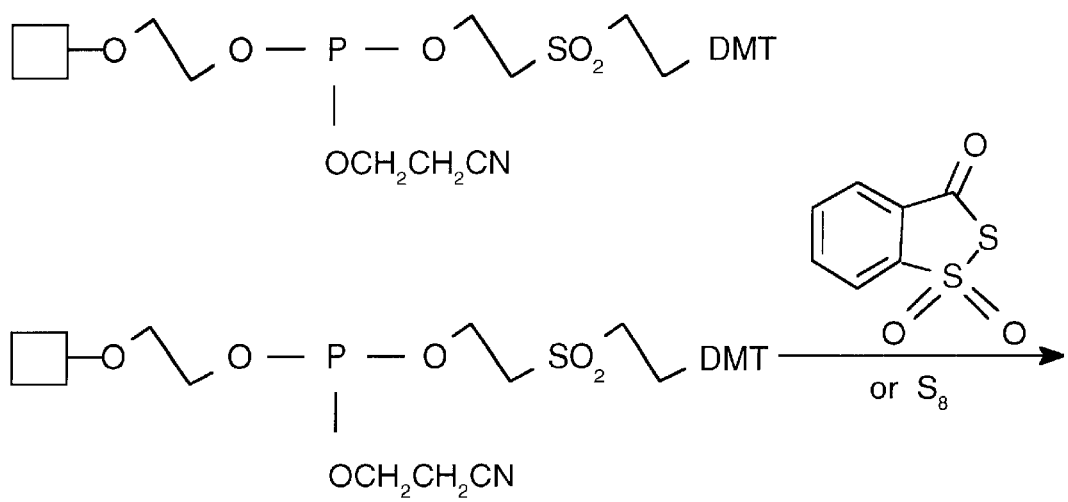
Figure 1:
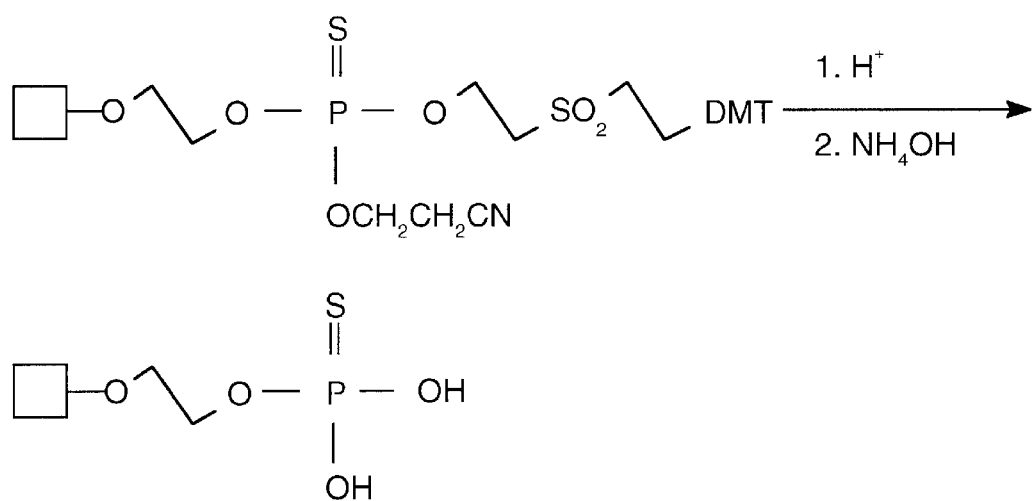

Preparation of a Solid Phase Quenching Agent that Contains a Thiophosphate Group The preparation of a solid phase quenching agent of the invention is described in FIG. 1. As shown, an aldehyde-activated Sepharose® bead (designated with a square) containing a hydroxyl group is derivatized with a phosphorylating agent. The phosphite group of the phosphorylated bead is oxidized to form a thiophosphate ester, which is cleaved with acid to provide a thiophosphate moiety. The product is a thiophosphate moiety that is attached to a Sepharose® bead through covalent bonds.

EXAMPLE 2

Quenching of an Aziridino Compound with a Thiosulfate or Thiophosphate Moiety that is Bound to a Separation Moiety A nucleophilic thiophosphate group, which is bound to a separation moiety, attacks and quenches the aziridino compound; the aziridino compound is not only rendered inactive, it also remains bonded to the quenching agent through covalent bonds.

EXAMPLE 3

Separation of Quenching Agent and Quenched Inactivating Agent from a Biological Composition By Filtration In one preferred method of the invention, the quenching moiety containing, for example, one or more thiosulfate or thiophosphate moieties) is covalently coupled to a bead or resin, such as Sepharose® or cellulose.

The bead has particular properties which allow for its separation from the biological composition. For example, Sepharose® beads can be separated, along with the quenching agent and the quenched inactivating agent, by filtration through a filter or column with the appropriate pore size (i.e., the pores are large enough to allow passage of the biologically-important molecules, but small enough to prevent passage of the beads). Suitable filters and columns can be purchased from, for example, Millipore Corp. (Bedford, Mass.).

EXAMPLE 4

Affinity-based Separation of Quenching Agent and Quenched Inactivating Agent from a Biological Composition By Filtration In one preferred variation, the method of the invention includes the coupling of two components. The first component includes a first quenching moiety attached to a second moiety. The second component includes a third moiety, which specifically binds to the second moiety, attached to a bead. In one example, the quenching moiety is attached to a biotin molecule, and then added to a biological composition (which had been virally inactivated with, for example, an ethyleneimine oligomer) for a length of time which allows for quenching of a viral inactivating agent. This biological composition is then passed through a column containing streptavidin-bound Sepharose®. The streptavidin specifically binds to the biotin-containing quenching agent. Hence, the biotinylated quenching agent, as well as the quenched inactivating agent, binds to the immobilized streptavidin, while the biological composition, now free of inactivating agent and quenching agent, flows through. It is understood that the streptavidin-bound Sepharose® can also be added to the biological composition, and subsequently removed through filtration, as described in Example 2, above. Similarly, other affinity-based methods can also be employed using other molecular pairs (e.g., an antigen-antibody pair, complementary nucleic acid sequences, or the like) replacing the streptavidin-biotin pair.

EXAMPLE 5

Separation of Quenching Agent and Quenched Inactivating Agent from a Biological Composition By Other Methods Those skilled in the art will recognize that there are numerous other variations which can be performed, and these variations are in the spirit of the invention. Quenching moieties bound to beads which contain iron can be separated, along with the quenched inactivating agent, by placing the biological composition in a magnetic field. Quenching moieties bound to beads having a mass substantially greater than that of biologically-important molecules can be separated by centrifugation. Moreover, these methods can be combined with the affinity-based methods described in Example 4. In one example, the quenching agent, attached to a biotin molecule, is added to a biological composition (which has been virally inactivated) for a length of time which allows for quenching of a viral inactivating agent. To this biological composition, iron-containing beads, coated with streptavidin, are added. The entire complex, including the quenched inactivating agent, is then separated from the biological composition by placing the biological composition in a magnetic field and transferring the biological composition to a second container.

In another example, quenched inactivating agent, as well as the quenching agent, can be removed by dialysis. The advantage of dialysis is that quenching agent, such as a thiosulfate or thiophosphate molecule can be removed, along with the quenched inactivating agent, whether the quenching agent is coupled to a separation moiety or not. The disadvantage is that dialysis, in contrast to the other methods of separation described herein, will not selectively remove the inactivating and quenching agents.

All publications and patents mentioned in this specification are herein incorporated by reference to the same extent as if each individual publication or patent was specifically and individually indicated to be incorporated by reference.

Other Embodiments

From the foregoing description, it will be apparent that variations and modifications may be made to the invention described herein to adopt it to various usages and conditions. Such embodiments are also within the scope of the following claims.

What is claimed is:

1. A method of inactivating a contaminant of a biological composition comprising the steps of:
   (a) contacting the biological composition with an inactivating agent, said agent comprising an aziridino moiety or a haloderivative salt thereof, where a portion of said agent reacts with and inactivates said contaminant, and a portion of said agent remains unreacted;
   (b) contacting the product of step (a) with a quenching agent comprising a quenching moiety, under conditions and for a time sufficient to allow said inactivating agent to bond covalently to said quenching moiety; and
   (c) separating said quenching agent and said quenched inactivating agent from the biological composition.

2. The method of claim 1, wherein said quenching moiety comprises a nucleophilic moiety selected from the group consisting of a thiophosphate moiety and a thiosulfate moiety.

3. The method of claim 2, wherein said thiophosphate moiety is part of an internucleotide linkage of an oligonucleotide sequence.

4. The method of claim 1, wherein said inactivating agent is selected from the group consisting of ethyleneimine, N-acetylethyleneimine, an ethyleneimine oligomer, a haloderivative salt of ethyleneimine, and a haloderivative salt of an ethyleneimine oligomer.

5. The method of claim 4, wherein said ethyleneimine oligomer is ethyleneimine dimer.

6. The method of claim 1, wherein said biological composition is selected from the group consisting of whole mammalian blood, purified or partially purified blood proteins, blood cell proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture supernatant, a placental extract, a product of fermentation, a platelet concentrate, a leukocyte concentrate, semen, red blood cells, and a recombinant protein-containing composition produced in a transgenic mammal.

7. The method of claim 6, wherein said biological composition is whole human blood or human blood plasma.

8. The method of claim 1, wherein said contaminant is a virus.

9. The method of claim 1, wherein said separating comprises the step of dialysis.

10. A method of inactivating a contaminant of a biological composition comprising the steps of:
    (a) contacting the biological composition with an inactivating agent, said agent comprising an aziridino moiety or a haloderivative salt thereof, where a portion of said agent reacts with and inactivates said contaminant, and a portion of said agent remains unreacted;
    (b) contacting the product of step (a) with a quenching agent comprising quenching moiety attached to a separation moiety through covalent bonds under conditions and for a time sufficient to allow said inactivating agent to bond covalently to said quenching moiety; and
    (c) separating said separation moiety, said quenching moiety and said quenched inactivating agent from the biological composition.

11. The method of claim 10, wherein said quenching moiety comprises a nucleophilic moiety selected from the group consisting of a thiophosphate moiety and a thiosulfate moiety.

12. The method of claim 11, wherein said thiophosphate moiety is part of an internucleotide linkage of an oligonucleotide sequence.

13. The method of claim 10, wherein said inactivating agent is selected from the group consisting of ethyleneimine, N-acetylethyleneimine, an ethyleneimine oligomer, a haloderivative salt of ethyleneimine, and a haloderivative salt of an ethyleneimine oligomer.

14. The method of claim 13, wherein said ethyleneimine oligomer is ethyleneimine dimer.

15. The method of claim 10, wherein said biological composition is selected from the group consisting of whole mammalian blood, purified or partially purified blood proteins, blood cell proteins, milk, saliva, blood plasma, platelet-rich plasma, a plasma concentrate, a precipitate from any fractionation of plasma, a supernatant from any fractionation of plasma, a serum, a cryoprecipitate, a cryosupernatant, a cell lysate, a mammalian cell culture, a mammalian culture supernatant, a placental extract, a product of fermentation, a platelet concentrate, a leukocyte concentrate, semen, red blood cells, and a recombinant protein-containing composition produced in a transgenic mammal.

16. The method of claim 15, wherein said biological composition is whole human blood or human blood plasma.

17. The method of claim 10, wherein said contaminant is a virus.

18. The method of claim 10, wherein said separation moiety is selected from the group consisting of a bead, a resin, an antibody, and a biotin molecule.

19. The method of claim 10, wherein said composition further comprises a reporter moiety selected from the group consisting of a UV adsorbing moiety and a fluorescent moiety.

* * * * *